(12) United States Patent
Sakuragi (10) Patent No.: US 10,182,782 B2
(45) Date of Patent: Jan. 22, 2019

(54) EVALUATION APPARATUS, EVALUATION METHOD, AND EVALUATION PROGRAM

(71) Applicant: FUJIFILM Corporation, Tokyo (JP)

(72) Inventor: Futoshi Sakuragi, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 4 days.

(21) Appl. No.: 15/439,432

(22) Filed: Feb. 22, 2017

(65) Prior Publication Data

US 2017/0245820 A1 Aug. 31, 2017

(30) Foreign Application Priority Data

Feb. 25, 2016 (JP) ................................ 2016-034001

(51) Int. Cl.
| | | |
|---|---|---|
| *G06K 9/00* | (2006.01) | |
| *A61B 6/00* | (2006.01) | |
| *A61B 34/10* | (2016.01) | |
| *A61B 5/055* | (2006.01) | |

(Continued)

(52) U.S. Cl.
CPC ............ *A61B 6/5217* (2013.01); *A61B 5/055* (2013.01); *A61B 6/032* (2013.01); *A61B 6/037* (2013.01); *A61B 34/10* (2016.02); *G06T 7/0012* (2013.01); *G06T 2207/10081* (2013.01); *G06T 2207/10088* (2013.01); *G06T 2207/10104* (2013.01)

(58) Field of Classification Search
CPC ......... A61B 34/10; A61B 5/055; A61B 6/032; A61B 6/037; A61B 6/5217; G06T 2207/10081; G06T 2207/10088; G06T 2207/10104; G06T 7/0012
See application file for complete search history.

(56) References Cited

U.S. PATENT DOCUMENTS

| | | | | |
|---|---|---|---|---|
| 6,496,188 B1 * | 12/2002 | Deschamps | .......... | G06K 9/4638 |
| | | | | 345/419 |
| 7,400,758 B2 * | 7/2008 | Shi | ........................ | G06T 7/0012 |
| | | | | 382/132 |
| 9,655,579 B2 * | 5/2017 | Sakuragi | ................ | A61B 6/032 |

(Continued)

FOREIGN PATENT DOCUMENTS

| | | |
|---|---|---|
| JP | 2009-95644 A | 5/2009 |
| JP | 2014-100555 A | 6/2014 |

OTHER PUBLICATIONS

T. Takamoto et al., "Planning of anatomical liver segmentectomy and subsegmentectomy with 3-dimensional simulation software", The American Journal of Surgery, 2013, vol. 206, pp. 530-538.

*Primary Examiner* — Avinash Yentrapati
(74) *Attorney, Agent, or Firm* — Birch, Stewart, Kolasch & Birch, LLP (57) ABSTRACT

A first extracting unit extracts at least one portion of a region of a target structure that includes lumen structures having branches from a three dimensional image of the target structure. A second extracting unit extracts the lumen structures from the at least one portion of the region of the target region. An index value calculating unit calculates an index value that represents the uniformity of the distribution of the lumen structures within the at least one portion of the region of the target structure, based on the at least one portion of the region of the target structure and the extracted lumen structures. Further, a quantifying unit quantifies the degree of reliability of the image quality of the at least one portion of the region of the target structure.

12 Claims, 4 Drawing Sheets

(51) Int. Cl.
*A61B 6/03* (2006.01)
*G06T 7/00* (2017.01)

(56) References Cited

U.S. PATENT DOCUMENTS

| | | | | |
|---|---|---|---|---|
| 2004/0151357 | A1* | 8/2004 | Shi | G06T 7/0012 |
| | | | | 382/131 |
| 2005/0240094 | A1* | 10/2005 | Pichon | G06T 7/60 |
| | | | | 600/407 |
| 2007/0249912 | A1* | 10/2007 | Tek | A61B 6/504 |
| | | | | 600/300 |
| 2008/0132774 | A1* | 6/2008 | Milstein | G06T 7/12 |
| | | | | 600/407 |
| 2008/0146929 | A1* | 6/2008 | Satoh | A61B 8/08 |
| | | | | 600/443 |
| 2008/0260226 | A1* | 10/2008 | Moriya | G06K 9/6201 |
| | | | | 382/128 |
| 2010/0266176 | A1* | 10/2010 | Masumoto | G06F 19/321 |
| | | | | 382/128 |
| 2015/0078648 | A1* | 3/2015 | Lee | G06K 9/0014 |
| | | | | 382/133 |
| 2015/0221089 | A1* | 8/2015 | Funabasama | A61B 6/032 |
| | | | | 382/130 |
| 2016/0063175 | A1* | 3/2016 | Choi | G06F 19/12 |
| | | | | 703/11 |

* cited by examiner

EVALUATION APPARATUS, EVALUATION METHOD, AND EVALUATION PROGRAM

CROSS REFERENCE TO RELATED APPLICATIONS

The present application claims priority under 35 U.S.C. § 119 to Japanese Patent Application No. 2016-034001 filed on Feb. 25, 2016. The above application is hereby expressly incorporated by reference, in its entirety, into the present application.

BACKGROUND

The present invention is related to a method, an apparatus, and a program for evaluating the image quality of target structures such as a liver, which is included in a three dimensional image.

Recently, pre surgical planning is being performed prior to performing surgical procedures. The pre surgical planning is performed by obtaining a three dimensional image generated from a plurality of tomographic images, such CT (Computed Tomography) images and MRI (Magnetic Resonance Imaging) images. Next, an organ which is to be the target of the surgical procedure is extracted from the three dimensional image. Then, the extracted organ is employed to execute the pre surgical planning to determine which portion of the organ is to be excised. Particularly, in the case that a structure having lumen structures in the interior thereof, such as the portal vein of the liver, is the target of the surgical procedure, the liver and the portal vein are extracted from the three dimensional image. Next, the dominated region of each branch of the portal vein is determined based on the distribution of the porta vein. Then, pre surgical planning is performed to determine the dominated region to be excised by the surgical procedure. Here, the dominated region refers to a region to which blood is supplied by portal veins toward the distal ends of branches, in the case of the liver.

In addition, the degree of reliability, which represents the appropriateness of pre surgical plans, is being evaluated by comparing the results of pre surgical plans, which are generated from three dimensional images obtained at medical facilities according to imaging conditions at each of the medical facilities, and the results of actual surgery (refer to T. Takamoto et. al., "Planning of anatomical liver segmentectomy and subsegmentectomy with 3-dimensional simulation software", The American Journal of Surgery, Vol. 206, Issue 4, pp 530-538, 2013).

In addition, a technique for calculating the degree of reliability of extraction results of organs and the like has also been proposed (refer to Japanese Unexamined Patent Publication No. 2009-98644). In this technique, statistical amounts, such as the average values of measured values of anatomical features (the lengths, the areas, the volumes, the shapes, the orientations, and the positional relationships) of organs and lumen structures, which are extracted from tomographic images, are obtained. Then, whether the statistical amounts are within ranges which are set in advance is judged. In addition, a technique that obtains statistical amounts such as average values from analysis results of images, and calculates the degree of reliability of the analysis results based on the statistical amounts has also been proposed (refer to Japanese Unexamined Patent Publication No. 2014-100555).

SUMMARY

There are cases in which the image quality of obtained three dimensional images will deteriorate, due to the influence of imaging conditions such as the amount of a contrast agent which is injected into lumen structures and imaging timings, in the case that target structures include lumen structures. If the image quality of a three dimensional image is poor, the image quality of a target structure will also be poor. As a result, the boundary of the target structure and the structure of lumen structures will become unclear. Therefore, the precision of extracting the target structure and lumen structures from the three dimensional image will deteriorate. For this reason, a possibility that a dominated region to be extracted is inappropriate will arise. In such cases, calculating the degree of reliability of the extraction results for the target structure and the lumen structures employing the techniques disclosed in Japanese Unexamined Patent Publication Nos. 2009-98644 and 2014-100555 may be considered. However, the techniques disclosed in Japanese Unexamined Patent Publication Nos. 2009-98644 and 2014-100555 do not take the relationship between target structures and lumen structures which are included in the target structures into consideration. Therefore, these techniques are not capable of accurately calculating the degree of reliability of extraction results for a target structure and lumen structures.

The present disclosure has been developed in view of the foregoing circumstances. The present disclosure enables the degree of reliability of extraction results for a target structure and lumen structures from a three dimensional image to be calculated accurately.

An evaluating apparatus of the present disclosure comprises:

a first extracting means configured to extract at least one portion of a region of a target structure from a three dimensional image of the target structure which includes lumen structures having branches;

a second extracting means configured to extract the lumen structures from the at least one portion of the region of the target structure; and an index value calculating means configured to calculate an index value that represents the uniformity of the distribution of the lumen structures within the at least one portion of the region of the target structure, based on the at least one portion of the region of the target structure and the extracted lumen structures.

The target structure includes therein the lumen structures having branches. The lumen structures should be uniformly distributed within the target structure which is extracted from the three dimensional image. However, in cases that the image quality of the three dimensional image is poor, the extraction results of the target structure are not favorable, or the like, an imbalance will be generated in the lumen structures within the target structure which is extracted from the three dimensional image, and the lumen structures will not be uniformly distributed within the target structure. The "index value that represents the uniformity of the distribution of the lumen structures within the at least one portion of the region of the target structure" is an index value at represents the degree to which the lumen structures are distributed without an imbalance within the at least one portion of the region of the target structure. The index value may indicate that the lumen structures are more uniformly distributed as the value thereof is greater, or may indicate that the lumen structures are more uniformly distributed as the value thereof is smaller.

The "at least one portion of a region of the target structure" may include the entire region of the target structure. For example, in the case that the target structure is a liver, the "at least one portion of a region of the target structure" may include the entire region of the liver. Alternatively, the "at least one portion of a region of the target structure" may include a portion of the region of the liver. An example of a portion of the region of the liver may be a region to be excised, which is determined by pre surgical planning, for example.

Note that in the evaluating apparatus of the present disclosure, the index calculating means may calculate the index value from regions other than a lesion within the at least one portion of the region of the target structure, in the case that a lesion is present within the at least one portion of the region of the target structure.

In addition, the evaluating apparatus of the present disclosure may further comprise a quantifying means configured to quantify at least one of the degree of reliability of the image quality of the at least one portion of the region of the target structure, the degree of reliability of the extraction results for the at least one portion of the region of the target structure, and the degree of reliability of the extraction results for the lumen structures, based on the index value.

In this case, if the at least one portion of the region of the target structure is a portion of a region determined within the target structure, the index value calculating means may calculate an index value that represents the distribution of lumen structures within the portion of the region; and the quantifying means may quantify the degree of reliability for the determined portion of the region within the target structure.

In addition, in the evaluating apparatus of the present disclosure, if the at least one portion of the region of the target structure is a portion of a region determined within the target structure, the index value calculating means may calculate an index value that represents the distribution of lumen structures within the portion of the region; and the evaluating apparatus may further comprise:

a quantifying means configured to quantify the degree of reliability for the determined portion of the region within the target structure.

In addition, in the evaluating apparatus of the present disclosure, the quantifying means may refer to a reliability map that defines relationships between index values and degree of reliability, to quantify the degree of reliability.

In this case, the reliability map may define the relationships between index values and degree of reliability, according to an allowable degree of error with respect to the at least one portion of the region of the target structure.

In addition, in the evaluating apparatus of the present disclosure, the index calculating means may calculate the shortest distance from each point within the at least one region of the region of the target structure to the lumen structures, and may calculate the index values based on the shortest distances.

In this case, the index value calculating means may calculate the index values based on a statistical value related to the shortest distances.

At least one of the average value, the maximum value, and the standard deviation of the shortest distances may be employed as the "statistical value related to the shortest distances".

The expression "calculate the index values based on a statistical value related to the shortest distances" means that the index values may be calculated to become greater as the statistical value related to the shortest distances is greater, or that the index values may be calculated to become greater as the statistical value related to the shortest distances is smaller. In the former case, the statistical value related to the shortest distances may be calculated as the index value, and in the latter case, the inverse of the statistical value related to the shortest distances may be calculated as the index value. In addition, the statistical value may be calculated by multiplying the statistical value or the inverse of the statistical value by an appropriate coefficient, to facilitate comparison among index values.

In addition, in the evaluating apparatus of the present disclosure, the index value calculating means may calculate the index value based on the percentage of the volume occupied by the lumen structures within the at least one portion of the region of the target structure.

In addition, in the evaluating apparatus of the present disclosure, the index value calculating means may calculate a threshold value to discriminate lumen structures and structures other than lumen structures with respect to the at least one portion of the region of the target structure, calculate the average value of pixel values within the at least one portion of the region of the target structure, and calculate the index value based on the difference between the threshold value and the average value.

In addition, in the evaluating apparatus of the present disclosure, the index value calculating means may calculate the index value based on the number of branches of the lumen structure within the at least one portion of the region of the target structure.

An evaluating method of the present disclosure comprises:

extracting at least one portion of a region of a target structure from a three dimensional image of the target structure which includes lumen structures having branches;

extracting the lumen structures from the at least one portion of the region of the target structure; and calculating an index value that represents the uniformity of the distribution of the lumen structures within the at least one portion of the region of the target structure, based on the at least one portion of the region of the target structure and the extracted lumen structures.

Note that the evaluating method of the present disclosure may be provided as a program that causes a computer to execute the evaluating method.

According to the present disclosure, at least one portion of a region of a target structure is extracted from a three dimensional image of the target structure which includes lumen structures having branches, and the lumen structures are extracted from the at least one portion of the region of the target structure. Then, an index value that represents the uniformity of the distribution of the lumen structures within the at least one portion of the region of the target structure is calculated, based on the at least one portion of the region of the target structure and the extracted lumen structures.

Here, the lumen structures having branches are uniformly distributed within the target structure. In the case that the lumen structures are extracted from the target structure, the lumen structures should be uniformly extracted throughout the entire region within the target structure. However, if the image quality of the three dimensional image is poor, the accuracy of extraction of the at least one portion of the region of the target structure is poor, the accuracy of extraction of the lumen structures is poor, or the like, there are cases in which the lumen structures cannot be uniformly extracted throughout the entirety of the at least one portion of the region of the target structure. In addition, in the case that a lesion is present within the target structure, the presence of the lesion will inhibit the spread of the lumen structures. For this reason as well, there are cases in which the lumen structures cannot be uniformly extracted throughout the entirety of the at least one portion of the region of the target structure if a lesion is present within the target structure.

The present disclosure calculates the index value that represents the uniformity of the distribution of the lumen structures within the at least one portion of the region of the target structure. Therefore, the degree of reliability of extraction results of the target structure and the lumen structures from within the three dimensional image can be accurately quantified based on the index value.

DETAILED DESCRIPTION OF THE PREFERRED EMBODIMENTS

Figure 1:
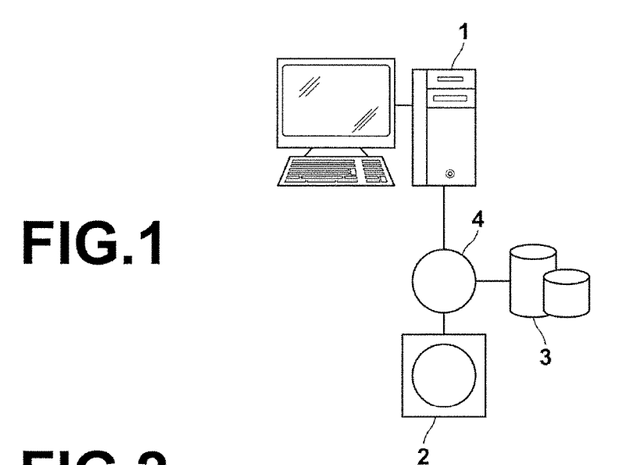
FIG. 1 is a diagram that illustrates the hardware configuration of a diagnosis assisting system to which n evaluating apparatus according to an embodiment of the present disclosure is applied.

Hereinafter, an embodiment of the present disclosure will be described with reference to the attached drawings. FIG. 1 is a diagram that illustrates the hardware configuration of a diagnosis assisting system to which n evaluating apparatus according to an embodiment of the present disclosure is applied. In this system, an evaluating apparatus 1 according to an embodiment of the present disclosure, a three dimensional image obtaining apparatus 2, and an image storage server 3 are connected via a network 4 such that the components are capable of communicating with each other, as illustrated in FIG. 1.

The three dimensional image obtaining apparatus 2 images a portion of a subject 7 which is a target of surgery, to generate a three dimensional image V0 that represents the portion of the subject 7. Specific examples of the three dimensional image obtaining apparatus 2 include a CT apparatus, an MRI apparatus, and a PET (Positron Emission Tomography) apparatus. The three dimensional image V0 which is generated by the three dimensional image obtaining apparatus 2 is transmitted to the image storage server 3 and stored therein. Note that in the present embodiment, the portion of the subject 7 which is the target of surgery is the liver, the three dimensional image obtaining apparatus 2 is a CT apparatus, and a three dimensional image V0 of the abdomen of the subject 7 is generated. Note that the liver, which is a target of surgery, is a target structure. In addition, the portal veins which are included in the liver are lumen structures.

The image storage server 3 is a computer that stores and manages various types of data, and is equipped with a large capacity external memory device and database management software. The image storage server 3 communicates with the other components of the system via a wired or a wireless network 4, to transmit image data and the like. Specifically, image data such as the three dimensional image V0 which is generated by the three dimensional image obtaining apparatus 2 are obtained via the network, then stored within a recording medium such as the large capacity external memory device and managed. Note that the storage format of image data and communications among each component of the system are based on a protocol such as the DICOM (Digital Imaging and Communication in Medicine) protocol.

The evaluating apparatus 1 is a single computer in which a evaluating program of the present disclosure is installed. The computer may be a work station or a personal computer which is directly operated by a physician who performs diagnosis, or may be a server computer connected to the work station or the personal computer via a network. The evaluating program is recorded on recording media such as a DVD (Digital Versatile Disc) and a CD-ROM (Compact Disc Read Only Memory) which are distributed, and installed onto the tablet terminal from the recording medium. Alternatively, the evaluating program is stored in a recording device of a server computer connected to a network or in a network storage, in a state accessible from the exterior, downloaded to the tablet terminal according to a request, then installed therein.

Figure 2:
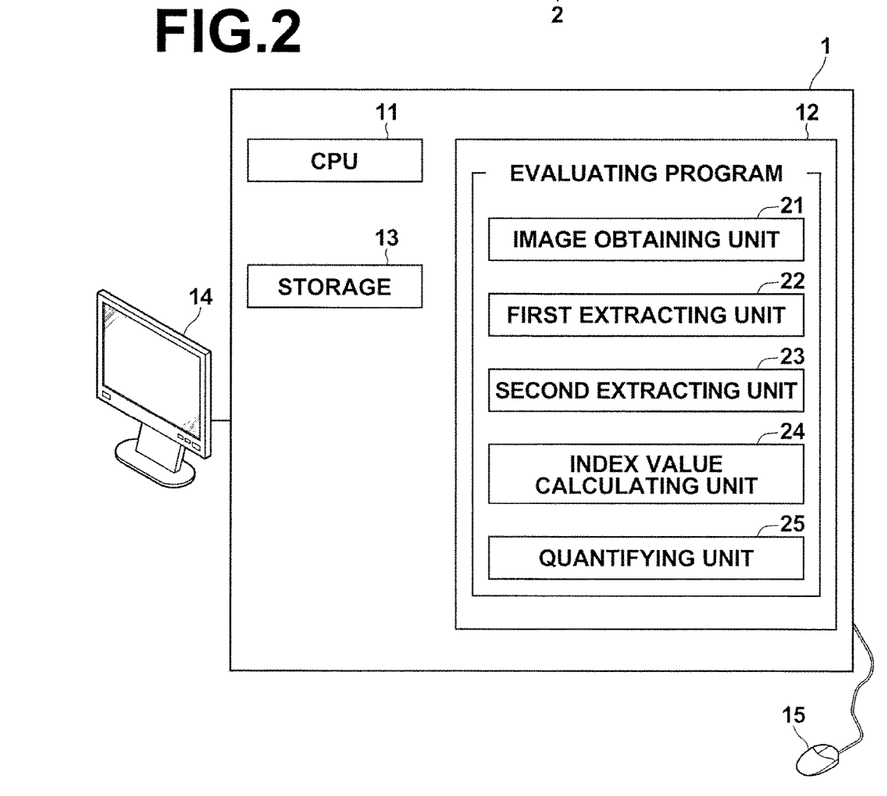
FIG. 2 is a schematic diagram that illustrates the configuration of an evaluating apparatus which is realized by installing an evaluating program in a computer.

FIG. 2 is a schematic diagram that illustrates the configuration of an evaluating apparatus which is realized by installing an evaluating program in a computer. As illustrated in FIG. 2, the position aligning apparatus 1 is equipped with a CPU (Central Processing Unit) 11, a memory 12, and a storage 13, as standard components of a computer. In addition, a display 14 and an input unit 15 such as a mouse are connected to the evaluating apparatus 1.

The storage 13 has recorded therein various types of data, including the three dimensional image V0 which is obtained from the image storage server 3 via the network 4, index values and the like which are generated by processes performed by the evaluating apparatus 1 as will be described later, and data necessary for the processes.

In addition, the evaluating program is stored in the memory 12. The evaluating program defines an image obtaining process that obtains the three dimensional image V0 obtained by the three dimensional image obtaining apparatus 2; a first extracting process that extracts at least one portion of a region of the liver from the three dimensional image V0; a second extracting process that extracts the portal veins, which are lumen structures, from the at least one portion of the region of the liver; an index value calculating process that calculates an index value that represents the degree of uniformity in the distribution of the portal veins within the at least one portion of the region of the liver, based on the portal veins which are extracted from the at least one portion of the region of the liver; and a quantifying process that quantifies at least one of the degree of reliability of the image quality of the at least one portion of the region of the liver, the degree of reliability of the extraction results for the at least one portion of the liver, and the degree of reliability of the extraction results for the portal veins.

The computer functions as an image obtaining unit 21, a first extracting unit 22, a second extracting unit 23, an index value calculating unit 24, and a quantifying unit 25, by the CPU executing the above processes according to the program. Note that the evaluating apparatus 1 may be equipped with a plurality of processors that execute each of the image obtaining process, the first extracting process, the second extracting process, the index value calculating process, and the quantifying process, respectively.

The image obtaining section 21 obtains the three dimensional image V0 from the image storage server. The image obtaining section 21 may obtain the three dimensional image V0 from the storage 13, if the three dimensional image V0 is already recorded in the storage 13.

The first extracting unit 22 extracts a liver, which is the target structure, from the three dimensional image V0. In the present embodiment, the extracting unit 22 extracts the entire region of the liver form the three dimensional image V0. Any method, such as a method in which a range of CT values for the liver within the three dimensional image V0 is estimated, a threshold value process is executed employing these values, ad a morphology filter is applied to a region extracted by the threshold value process, may be employed to extract the liver. Alternatively, a method in which a plurality of liver phase images which are obtained in temporal series is employed to extract an imaged pattern of the liver region, and the liver region is extracted employing the imaged pattern, as disclosed in "Method for Automatically Extracting Liver Region from Multiple CT Images of the Abdomen at Multiple Temporal Phases by Applying Non Rigid Registration", Journal of the Academy of Computer Assisted Image Diagnosis, Vol. 7, No. 4-1, June 2003. As a further alternative, the level set method as disclosed in "A Liver Level Set (LLS) Algorithm for Extracting Liver's Volume Containing Disconnected Regions Automatically", IJCSNS International Journal of Computer Science and Network Security, Vol. 8, No. 12, December 2008 and "Development and Evaluation of Liver Region Extracting Methods that Employ the Level Set Method", Journal of the Academy of Computer Assisted Image Diagnosis, Vol. 7, No. 4-2, June 2003 may be employed. Note that as a still further alternative, a user may extract a liver region from the three dimensional image V0 by manual operations.

The second extracting unit 23 extracts portal veins from the liver which is extracted by the first extracting unit. Examples of methods for extracting the portal veins include a method in which position data and major axis directions of a plurality of candidate points that represent a target structure constituted by linear structures are calculated, and the plurality of candidate points are reconstructed such that they are connected to each other by employing a cost function having variables based on the calculated position data and major axis directions as disclosed in Japanese Unexamined Patent Publication No. 2010-220742 and a method that automatically discriminates and extracts blood vessels as disclosed in Japanese Unexamined Patent Publication No. 2011-212314. Alternatively, the histogram analysis may be administered on the pixel values (CT values) of the liver which is extracted by the first extracting unit 22, a threshold value may be calculated to discriminate portal veins and other structures, and the portal veins may be extracted employing the calculated threshold value. Note that as a further alternative, a user may extract the portal veins by manual operations.

The index value calculating unit 24 calculates an index value that represents the degree of uniformity of the distribution of the portal veins within the liver, based on the extracted liver and portal veins. In the present embodiment, a distance image of the liver is generated employing the portal veins, and the index value is calculated based on a statistical value related to the distance values through the entirety of the liver. Specifically, the index value calculating unit 24 calculates the shortest distances from the portal veins at each point within the liver, and calculates the inverse of the statistical value as the index value. The statistical value may be at least one of the average value, the maximum value, and the standard deviation of the shortest distances. Hereinafter, calculation of the index value will be described.

Figure 3:
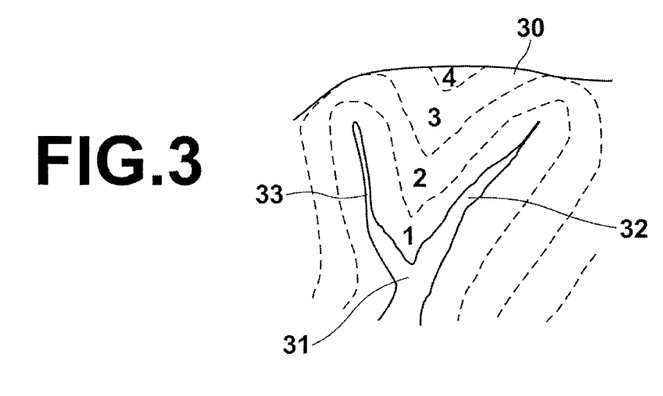
FIG. 3 is a diagram for explaining calculation of an index value.
Figure 4:
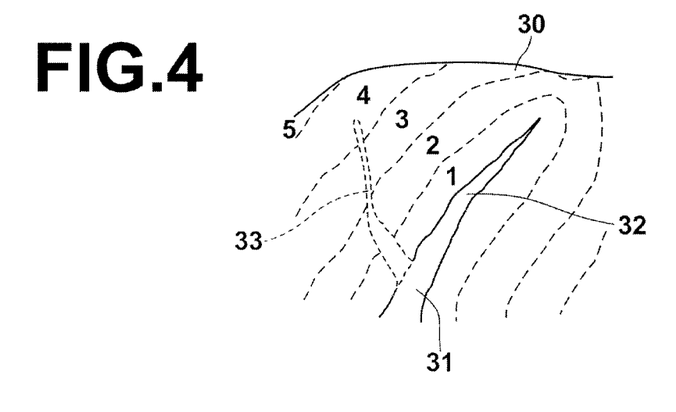
FIG. 4 is a diagram for explaining calculation of an index value.

FIG. 3 and FIG. 4 are diagrams for explaining how the index value is calculated. FIG. 3 illustrates a state in which portal veins 32 and 33 branch from a branching position 31 and are uniformly distributed within the liver region. In addition, FIG. 3 illustrates the range of the distances from the surfaces of the portal veins 32 and 33 from each point within the liver 30 as broken contour lines. Note that the numerical values indicated as the range of shortest distances represent the distances from the surfaces of the portal veins 32 and 33. The distances are greater as the numerical values are greater.

Here, as illustrated in FIG. 4, assume that the portal vein 33 is not extracted within the region of the same liver as that illustrated in FIG. 3 for a reason such as the image quality of the liver being poor, the accuracy of portal vein extraction being low, etc. In this case, the index value calculating unit 24 calculates the shortest distances based only on the portal vein 32. The values of the shortest distances at positions which are close to the portal vein 33 will become those to the portal 32, and therefore will be greater than those illustrated in FIG. 3. For example, in the case that the portal vein 33 is extracted, the maximum value of the shortest distances is 4. However, in the case that the portal vein 33 is not extracted, the maximum value of the shortest distances is 5. As a result, the statistical value which is calculated based on the shortest distances will become greater for a case in which the portal vein 33 is not extracted. In the present embodiment, the index value calculating unit 24 calculates the inverse of the calculated statistical value as the index value such that the index value becomes greater as the degree of uniformity of the distribution of the portal veins within the liver is higher. Accordingly, the statistical value becomes smaller as the degree of uniformity of the distribution of the portal veins within the liver is higher, and the index value becomes greater.

Figure 5:
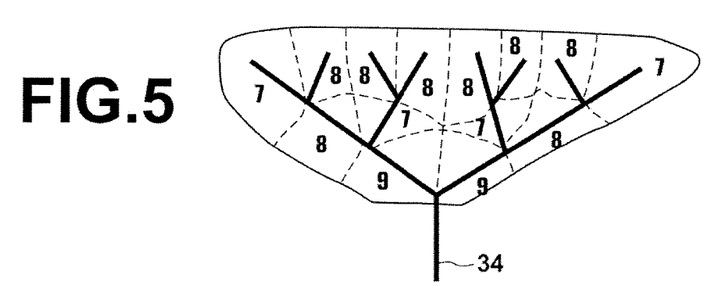
FIG. 5 is a diagram for explaining calculation of an index value for each of a plurality of dominated regions.
Figure 6:
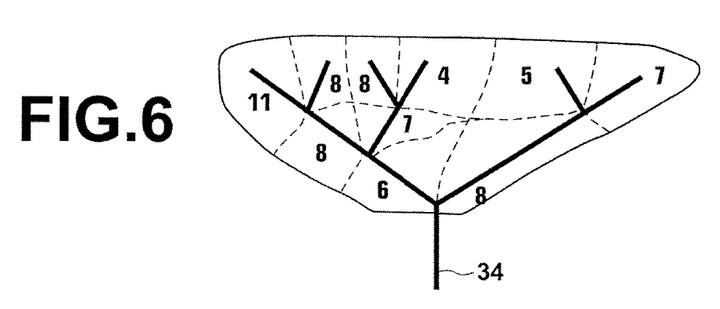
FIG. 6 is a diagram for explaining calculation of an index value for each of a plurality of dominated regions.

Meanwhile, in the present embodiment, the index value calculating unit 24 extracts the cores of the extracted portal veins, determines the dominated regions of the portal veins in units of branches, and calculates the inverse of the statistical value related to the shortest distances from each point within a dominated region to the portal veins for each of the dominated regions. FIG. 5 and FIG. 6 are diagrams for explaining calculation of index values for each dominated region. Note that in FIG. 5 and FIG. 6, the dominated regions are determined by Voronoi tessellation employing portal veins 34 as a reference according to the technique disclosed in Japanese Unexamined Patent Publication No. 2003-033349, for example. In addition, FIG. 5 and FIG. 6 illustrate calculation results for index values that employ the inverses of statistical values, which are calculated for each dominated region from the shortest distances from each point within the liver region to the portal veins 34. Note that in the present embodiment, the index values are calculated by multiplying the inverses of statistical values by a constant, in order to facilitate comparison of index values among a plurality of dominated regions. Here, if the portal veins 34 are uniformly distributed within the liver, the differences among the index values of the dominated regions will not be great, as illustrated in FIG. 5. In contrast, in the case that the portal veins are not uniformly distributed within the liver due to not all of the portal veins being extracted or the like, the index values will become smaller for dominated regions in which the portal veins are not uniformly distributed. Therefore, the difference among index values of the dominated regions will become greater, as illustrated in FIG. 6.

Note that the index value calculating unit 24 may calculate the ratio of the volume of the extracted portal veins to the volume of the extracted liver as the index value. In this case, the index value will become greater as the degree of uniformity of the distribution of the portal veins within the liver is higher. In addition, the ratio of the volume of the extracted portal veins to the volume of the extracted liver as the index value in the case that the index value is calculated for each of a plurality of dominated regions as well.

As another alternative, the index value calculating unit 24 may calculate the index value based on the difference between the threshold value, which is calculated by the second extracting unit 23 to discriminate the portal veins and other regions when extracting the portal veins by histogram analysis, and the average value of pixel values within the entirety of the liver. In this case, the threshold value will become closer to the average value of the pixel values within the entirety of the liver as the degree of uniformity of the distribution of the portal veins within the liver is higher. Therefore, the difference will become smaller in the case that the portal veins are uniformly distributed within the liver, and will become greater in cases that not all of the portal veins are extracted or the like. For this reason, the index value calculating unit 24 calculates the inverse of the calculated difference as the index value such that the index value becomes greater as the degree of uniformity of the distribution of the portal veins within the liver is higher. In addition, the difference between the threshold value and the average value which is employed for histogram analysis may be employed as the index value in the case that index values are calculated for each of a plurality of dominated regions as well.

As a further alternative, the index value calculating unit 24 may calculate the index value based on the number of branching positions in the portal veins within the liver. In this case, if the portal veins are uniformly distributed within the liver, the number of branching positions will be great, and the number of branching positions will be small in the case that not all of the portal veins are extracted or the like. For this reason, the index value calculating unit 24 calculates the number of branching positions itself as the index value. In addition, the number of branching positions may be employed as the index value in the case that index values are calculated for each of a plurality of dominated regions as well.

Note that it is preferable for the index value calculating unit 24 to calculate the index value from regions other than a lesion region within the liver, in the case that a lesion is present within the liver. In this case, a lesion region may be specified by receiving input from a user, or specified by employing a known CAD (Computer Aided Diagnosis) technique. In this case, the evaluating apparatus of the present embodiment will be equipped with an additional means configured to extract a lesion. In the case that a lesion region is present, it is difficult for portal veins to be distributed within the lesion region, and therefore the portal veins will not be extracted. For this reason, the index value can be accurately calculated without being influenced by the lesion region, by calculating the index value from regions other than the lesion region. Note that in the present embodiment, the index value is calculated without excluding the lesion region in the case that index values are calculated for each of a plurality of dominated regions in order to quantify the degree of reliability of the extraction results of the portal veins, as will be described later.

The quantifying unit 25 quantifies at least one of the degree of reliability of the image quality of the liver, the degree of reliability of the extraction results for the liver, and the degree of reliability of the extraction results for the portal veins, based on the index value. In the present embodiment, all of the degree of reliability of the image quality of the liver, the degree of reliability of the extraction results for the liver, and the degree of reliability of the extraction results for the portal veins are quantified. First, quantification of the degree of reliability of the image quality of the liver will be described.

Figure 7:
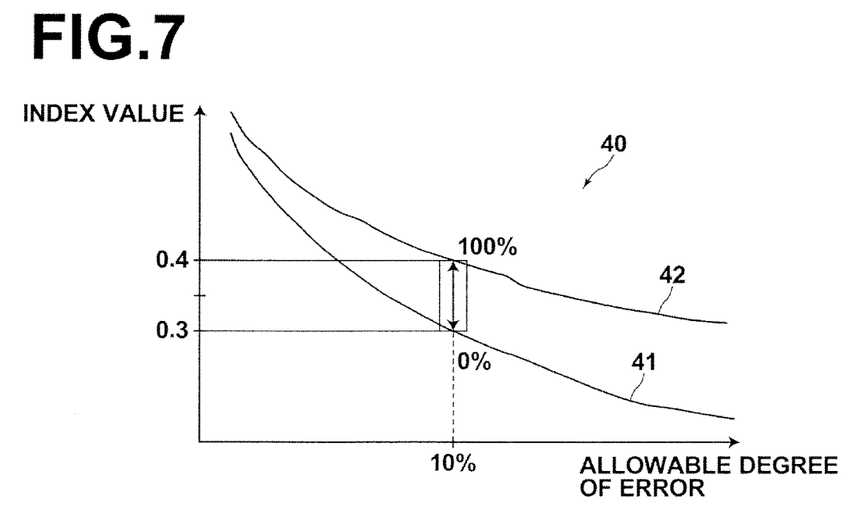
FIG. 7 is a diagram that illustrates a reliability map.

The quantifying unit 25 quantifies the degree of reliability employing a reliability map, which is prepared in advance and stored in the storage 13. FIG. 7 is a diagram that illustrates the reliability map. As illustrated in FIG. 7, the reliability map 40 has allowable errors defined along the horizontal axis, and index values defined along the vertical axis. The degree of reliability is greater as the allowable error is smaller and the index value is greater. In addition, the reliability map defines a monotonously decreasing curve 41 that indicates a degree of reliability of 0% and a monotonously decreasing curve 42 that defines a degree of reliability of 100%. The reliability map defines degrees of reliability such that when index values are plotted with respect to a specified allowable error, the degree of reliability is 0% if the plotted position is lower than the curve 41 and 100% if the plotted position is above the curve 42. In addition, the reliability map defines degrees of reliability such that if the plotted position is between the curve 41 and the curve 42, the degree of reliability is quantified as a percentage according to the plotted position.

Here, the degree of reliability of the image quality of the liver represents to what degree of reliability the image quality of the liver exhibits for utilization as an image for diagnosis or surgical planning. If the image quality of the liver, that is, the image quality of the three dimensional image V0, is favorable, the liver and the portal veins can be accurately extracted. As a result, the portal veins will be uniformly distributed within the liver, and therefore the index value will become greater. Conversely, if the image quality of the three dimensional image V0 is poor, the liver and the portal veins will not be accurately extracted. As a result, the portal veins will not be uniformly distributed within the liver, and therefore the index value will become smaller. Note that the allowable degree of error is set by a physician who is a user, and is set according to a degree of error desired by the user. For example, in the case that stringent requirements regarding errors are desired with respect to the image quality, the allowable degree of error is set to be smaller, and in the case that it is not necessary for requirements regarding errors to be as stringent, the allowable degree of error is set to be greater. The allowable degree of error is input via the input unit 15.

FIG. 7 illustrates calculation of the degree of reliability for a case in which the allowable degree of error is set to 10%. As illustrated in FIG. 7, in the case that the allowable degree of error is set to 10%, the degree of reliability will be 0% if the index value is 0.3, and 100% if the index value is 0.4. The quantifying unit 25 refers to the reliability map 40 based on the index value calculated by the index value calculating unit 24 and the allowable degree of error, to quantify the degree of reliability. For example, if the allowable degree of error is set to 10% and the index value is 0.35 in the reliability map 40 illustrated in FIG. 7, the degree of reliability will be quantified to be 50%. Note that the quantified degree of reliability is displayed on the display 14 as a numerical value. In this case, the reliability map 40 may be displayed along with the numerical value.

Here, reliability maps 40 that quantify the degree of reliability of the extraction results of the liver and the degree of reliability of the extraction results of the portal veins are prepared and stored in the storage 13, in addition to the reliability map that quantifies the degree of reliability of the image quality of the liver. In the case that the quantifying unit 25 calculates the degree of reliability of the extraction results of the liver, the reliability map for calculating the degree of reliability of the extraction results of the liver is referred to, to calculate the degree of reliability of the extraction results of the liver. The calculated degree of reliability of the extraction results of the liver is displayed on the display 14 in the same manner as the degree of reliability of the image quality of the liver.

Note that a user may view the degrees of reliability of the image quality and the extraction results of the liver which are displayed on the display 14, to judge whether the image quality of the liver as well as three dimensional image V0 are favorable. In addition, the user may view the degrees of reliability of the image quality and the extraction results of the liver which are displayed on the display 14 to judge whether the algorithm for extracting the liver is favorable. In the case that the user determines that the algorithm for extracting the liver is not favorable, measures such as reobtaining an image may be taken in the case that the cause is the image quality. Meanwhile, in the case that the cause is in the algorithm for extracting the liver, measures, such as changing the parameters of the algorithm and re-extracting the liver by manual operations may be taken. Note that in the present embodiment, lesion regions are excluded when quantifying the degrees of reliability of the image quality and the extraction results of the liver. Therefore, the user may perform the aforementioned judgments without taking the influence of lesions into consideration. In the case that the user determines that the image quality of the liver is not favorable, measures such as reobtaining an image may be taken.

Meanwhile, with respect to the degree of reliability of the extraction results of the portal veins, the quantifying unit 25 may quantify the degree of reliability by normalizing the index values, which are calculated by the index value calculating unit 24 for each of a plurality of dominated regions, by a predetermined value. In this case, the predetermined value may be a standard index value within the liver and a range of index values. Note that the predetermined value is input via the input unit 15 and is stored in the storage 13.

Here, in the case that the index value is calculated based on a statistical value, as well as in the case that the index value is calculated based on a histogram, the index value does not depend on the number of branching positions up to dominated regions or the distance from the root of the portal vein to the dominated regions. In contrast, in the case that the index value is the ratio of the volume of the portal veins with respect to the volume of the liver, the index value for each dominated region depends on the distance from the root of the portal vein to the dominated regions. In this case, it is preferable for the predetermined value for normalizing the index values to be set such that they change according to the distances from the root of the portal vein to the dominated regions. Note that the distances from the root of the portal vein to the dominated regions may be normalized by the length of the portal veins from the root of the portal vein to the dominated region farthest from the root, the volume of the entirety of the liver, or the length of the longest portion of the liver, and employed to normalize the index values. Here, the distance from the edge of the left lobe to the edge of the right love of the liver as viewed from the front may be employed as the length of the longest portion of the liver.

Figure 8:
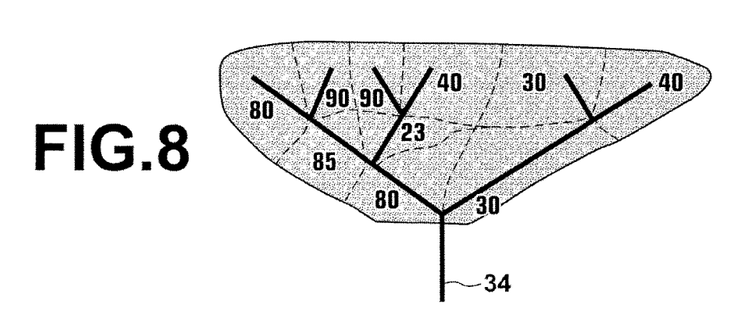
FIG. 8 is a diagram that illustrates the degree of reliability of extraction results of a displayed portal vein.

The quantifying unit 25 displays the degrees of reliability which are quantified in these manners on the display 14. FIG. 8 is a diagram that illustrates displayed degrees of reliability of the extraction results for the portal veins. Note that FIG. 8 illustrates degrees of reliability which are quantified based on the index values which are calculated as illustrated in FIG. 6. As illustrated in FIG. 8, degrees of reliability, which are quantified for each of a plurality of dominated regions within the liver, are displayed on the display 14. Note that the inverse of a statistical value may be calculated as the index value for each dominated region, and the degree of reliability for each dominated region may be quantified by applying the reliability map illustrated in FIG. 7.

A user may view the degrees of reliability of the extraction results for the portal veins which are displayed on the display 14, to judge whether the algorithm for extracting the portal veins is favorable. Note that in the present embodiment, lesion regions are not excluded when quantifying the degrees of reliability of the extraction results for the portal veins. Therefore, the possibility of the presence of lesion regions can also be judged by viewing the degrees of reliability of the extraction results for the portal veins which are displayed on the display 14. Particularly in the case that a lesion region is extracted and a user is aware of the position thereof, the position of the lesion can be confirmed. As a result, the degrees of reliability of the extraction results for the portal veins can be judged without considering the influence of lesions. In the case that the user judges that the algorithm for extracting the portal veins is not favorable, measures such as reobtaining an image may be taken in the case that the cause is considered to be the image quality. Meanwhile, in the case that the cause is in the algorithm for extracting the portal veins, measures, such as changing the parameters of the algorithm and re-extracting the portal veins by manual operations may be taken.

Further, the user may view the degrees of reliability of the extraction results for the portal veins which are displayed on the display 14, to determine a dominated region to be ultimately surgically excised. For example, in the case that the position of a lsoin is known, a dominated region that includes the lesion is determined to be the dominated region to be excised. In the case that the position of a lesion is not known, a dominated region, in which the degree of reliability of the extraction result for the portal vein is low, is determined to be the dominated region to be excised. The quantifying unit 25 refers to an index value of the determined dominated region, an allowable degree of error, and a reliability map for dominated regions, to quantify a degree of reliability for the determined dominated region. In this case, the index value may be the index value which is calculated by the index value calculating unit 24 for each dominated region when quantifying the degrees of reliability of the extraction results for the portal veins. Note that the index value calculating unit 24 may recalculate an index value for the dominated region which is determined to be excised, and the quantifying unit 25 may quantify a degree of reliability employing the recalculated index value. The quantifying unit 25 displays the quantified degree of reliability on the display 14.

The user may view the degree of reliability for the dominated region to determine whether the dominated region to be excised is appropriate. In the case that the degree of reliability for the dominated region is low, the user may reset the dominated region to be excised. Thereafter, the index value calculating unit 24 may recalculate an index value for the dominated region which is determined to be excised again, and the quantifying unit 25 may quantify a degree of reliability employing the recalculated index value.

Figure 9:
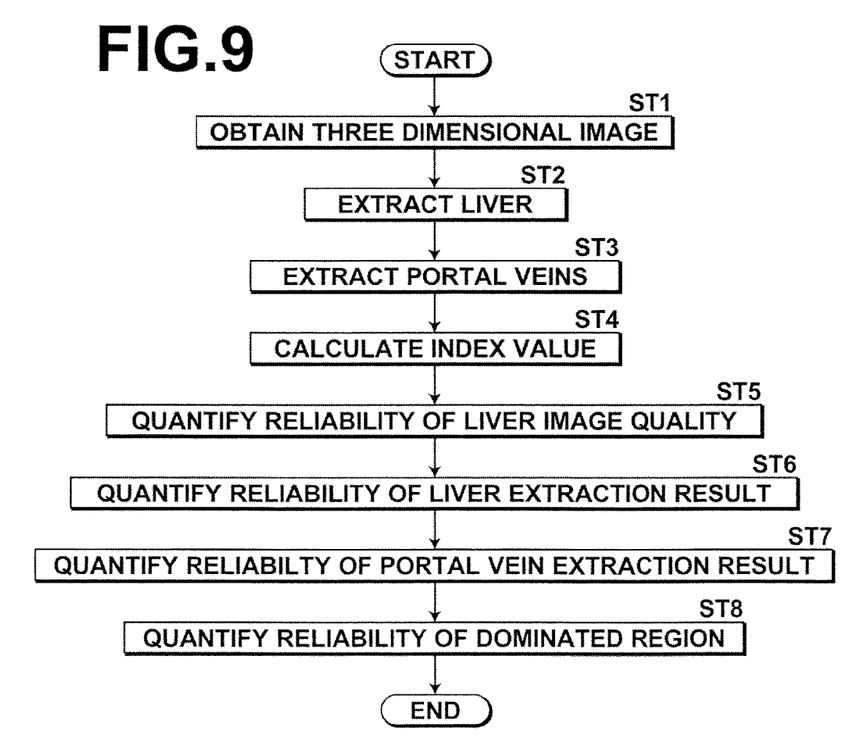
FIG. 9 is a flow chart that illustrates the processes which are performed by the present embodiment.

Next, the processes which are performed by the present embodiment will be described. FIG. 9 is a flow chart that illustrates the processes which are performed by the present embodiment. First, the image obtaining unit 21 obtains a three dimensional image V0 (step ST1), and the first extracting unit 22 extracts a liver, which is a target structure, from the three dimensional image V0 (step ST2). Next, the second extracting unit 23 extracts portal veins from the liver (step ST3). Further, the index value calculating unit 24 calculates an index value that represents the uniformity of the distribution of the portal veins within the liver (step ST4). Then, the quantifying unit 25 quantifies the degree of reliability of the image quality of the liver (step T5), quantifies the degree of reliability of the extraction results of the liver (step ST6), and quantifies the degree of reliability of the extraction results of the portal veins (step ST7). Note that the order in which steps ST5 through ST7 are performed may be changed as appropriate, or these steps may be performed in parallel. Further, the quantifying unit 25 quantifies the degree of reliability of a dominated which is determined to be excised (step ST8), and the process ends.

As described above, present the embodiment calculates the index value that represents the uniformity of the distribution of the portal veins within the liver or the index values that represent the uniformity of the distribution of the portal veins within dominated regions of the liver. Therefore, the degree of reliability of the image quality of the liver, the degree of reliability of the extraction results of the liver, the degree of reliability of the extraction results of the portal veins, and the degree of reliability of the dominated region can be accurately quantified, based on the index values.

Note the embodiment described above quantifies the degree of reliability of the image quality of the liver, the degree of reliability of the extraction results of the liver, the degree of reliability of the extraction results of the portal veins, and the degree of reliability of the dominated region. However, only one or two of the above degrees of reliability may be quantified.

In addition, the degree of reliability of the extraction results for the portal veins is quantified in the embodiment described above. However, the evaluating apparatus of the present disclosure may be configured to display only the index values which are calculated for each of the dominated regions on the display 14, as illustrated in FIG. 5 and FIG. 6. In this case, a user who views the displayed index values may determine the degree for reliability of the extraction results for the portal veins.

In addition, in the embodiment described above, the legion region is excluded when calculating the degrees of reliability of the image quality and the extraction results of the liver. Alternatively, the degrees of reliability of the image quality and the extraction results of the liver may be calculated without excluding the lesion region. In this case, the possibility of the presence of a lesion can be evaluated in addition to the degrees of reliability of the image quality and the extraction results of the liver.

In addition, in the embodiment described above, the lesion region is not excluded when calculating the degree of reliability of the extraction results for the portal veins. Alternatively, the lesion region may be excluded when calculating the degree of reliability of the extraction results for the portal veins. In this case, the degree of reliability of the extraction results for the portal veins may be calculated without evaluating the possibility of the presence of a lesion.

In addition, in the embodiment described above, the three dimensional image V0 may be employed to determine a dominated region to be excised, and the degree of reliability of the dominated region may be quantified only for the dominated region which is determined to be excised.

In addition, in the embodiment described above, the target structure and the lumen structure are the liver and the portal vein. However, the present disclosure is not limited to such a configuration. The present displeasure may evaluate degrees of reliability for target structures in which lumen structures are uniformly distributed. Examples of such target structures and lumen structures include a lung and bronchial tubes, as well as a brain and blood vessels within the brain.

The operative effects of the present embodiment will be described below.

In the case that a lesion region is present within at least one portion of a region of a target structure, calculating the index value after extracting the lesion region from the at least one portion of the region of the target structure enables the legion region to be excluded. Therefore, the index value can be calculated accurately, without being influenced by the presence of a lesion.

At least one of the degree of reliability of the image quality, the degree of reliability of the extraction results of the at least one portion of the region of the target structure, and the degree of reliability of the extraction results of the lumen structures is quantified based on the index values. Thereby, these degrees of reliability can be obtained.

Quantifying the degrees of reliability by referring to the reliability maps that define the relationships among index values and degrees of reliability enables the degrees of reliability to be quantified easily.

What is claimed is:

1. An evaluating apparatus comprising:
   processor configured to:
   extract at least one portion of a region of a target structure from a three dimensional image of the target structure which includes lumen structures having branches;
   extract the lumen structures from the at least one portion of the region of the target structure;
   calculate an index value that represents the uniformity of the distribution of the lumen structures within the at least one portion of the region of the target structure, based on the at least one portion of the region of the target structure and the extracted lumen structures; and
   quantify at least one of the degree of reliability of the image quality of the at least one portion of the region of the target structure, the degree of reliability of the extraction results for the at least one portion of the region of the target structure, and the degree of reliability of the extraction results for the lumen structures, based on the index value,
   wherein the processor refers to a reliability map that defines relationships between index values and degree of reliability, to quantify the degree of reliability.

2. An evaluating apparatus as defined in claim 1, wherein:
   the processor calculates the index value from regions other than a lesion region within the at least one portion of the region of the target structure, in the case that a lesion region is present within the at least one portion of the region of the target structure.

3. An evaluating apparatus as defined in claim 1, wherein:
if the at least one portion of the region of the target structure is a portion of a region determined within the target structure, the processor calculates an index value that represents the distribution of lumen structures within the portion of the region; and
the processor is further configured to quantify the degree of reliability for the determined portion of the region within the target structure.

4. An evaluating apparatus as defined in claim 1, wherein:
if the at least one portion of the region of the target structure is a portion of a region determined within the target structure, the processor calculates an index value that represents the distribution of lumen structures within the portion of the region; and
the processor quantifies the degree of reliability for the determined portion of the region within the target structure.

5. An evaluating apparatus as defined in claim 1, wherein:
the reliability map defines the relationships between index values and degree of reliability, according to an allowable degree of error with respect to the at least one portion of the region of the target structure.

6. An evaluating apparatus as defined in claim 1, wherein:
the processor calculates the shortest distance from each point within the at least one region of the region of the target structure to the lumen structures, and calculates the index values based on the shortest distances.

7. An evaluating apparatus as defined in claim 6, wherein:
the processor calculates the index values based on a statistical value related to the shortest distances.

8. An evaluating apparatus as defined in claim 1, wherein:
the processor calculates the index value based on the percentage of the volume occupied by the lumen structures within the at least one portion of the region of the target structure.

9. An evaluating apparatus as defined in claim 1, wherein:
the processor calculates a threshold value to discriminate lumen structures and structures other than lumen structures with respect to the at least one portion of the region of the target structure, calculates the average value of pixel values within the at least one portion of the region of the target structure, and calculates the index value based on the difference between the threshold value and the average value.

10. An evaluating apparatus as defined in claim 1, wherein:
the processor calculates the index value based on the number of branches of the lumen structure within the at least one portion of the region of the target structure.

11. An evaluating method, comprising:
extracting at least one portion of a region of a target structure from a three dimensional image of the target structure which includes lumen structures having branches;
extracting the lumen structures from the at least one portion of the region of the target structure;
calculating an index value that represents the uniformity of the distribution of the lumen structures within the at least one portion of the region of the target structure, based on the at least one portion of the region of the target structure and the extracted lumen structures; and
quantifying at least one of the degree of reliability of the image quality of the at least one portion of the region of the target structure, the degree of reliability of the extraction results for the at least one portion of the region of the target structure, and the degree of reliability of the extraction results for the lumen structures, based on the index value,
wherein in quantifying the degree of reliability, a reliability map that defines relationships between index values and degree of reliability is referred to.

12. A non-transitory recording medium having an evaluating program recorded therein, the evaluating program causing a computer to execute the procedures of:
extracting at least one portion of a region of a target structure from a three dimensional image of the target structure which includes lumen structures having branches;
extracting the lumen structures from the at least one portion of the region of the target structure;
calculating an index value that represents the uniformity of the distribution of the lumen structures within the at least one portion of the region of the target structure, based on the at least one portion of the region of the target structure and the extracted lumen structures; and
quantifying at least one of the degree of reliability of the image quality of the at least one portion of the region of the target structure, the degree of reliability of the extraction results for the at least one portion of the region of the target structure, and the degree of reliability of the extraction results for the lumen structures, based on the index value,
wherein in quantifying the degree of reliability, a reliability map that defines relationships between index values and degree of reliability is referred to.

* * * * *